United States Patent [19]

Bader et al.

[11] Patent Number: 5,100,673

[45] Date of Patent: Mar. 31, 1992

[54] MICROENCAPSULATION OF BIOLOGICALLY ACTIVE MATERIAL

[75] Inventors: Hebert Bader, Mainz; Karl-Heinz Keil, Hanaub; Diether Rüppel; Merten Schlingmann, Königstein/Taunus, Fed. Rep. of Germany; Axel Walch, Frankfurt am Main, all of Fed. Rep. of Germany

[73] Assignee: Hoechst Aktiengesellschaft, Frankfurt am Main, Fed. Rep. of Germany

[21] Appl. No.: 483,984

[22] Filed: Feb. 21, 1990

Related U.S. Application Data

[63] Continuation of Ser. No. 159,396, Feb. 23, 1988, abandoned.

[30] Foreign Application Priority Data

Feb. 25, 1987 [DE] Fed. Rep. of Germany ....... 3706010

[51] Int. Cl.$^5$ .................. A61K 9/48; A61K 31/74
[52] U.S. Cl. ...................... 424/451; 424/78; 424/79; 424/456
[58] Field of Search .................. 424/451, 456

[56] References Cited

U.S. PATENT DOCUMENTS

| | | | |
|---|---|---|---|
| 3,069,370 | 12/1962 | Jensen et al. | 252/316 X |
| 3,594,327 | 7/1971 | Becsey | 252/316 |
| 4,449,983 | 5/1984 | Cortese et al. | 424/424 X |
| 4,585,652 | 4/1986 | Miller | 424/424 X |
| 4,663,149 | 5/1987 | Eckenhoff et al. | 424/456 X |
| 4,789,516 | 12/1988 | Lim | 424/424 X |
| 4,795,642 | 1/1989 | Cohen et al. | 424/456 X |

FOREIGN PATENT DOCUMENTS

| | | |
|---|---|---|
| 0129619 | 1/1985 | European Pat. Off. |
| 0152898 | 8/1985 | European Pat. Off. |
| 0188309 | 7/1986 | European Pat. Off. |
| 2135954A | 9/1984 | United Kingdom |

OTHER PUBLICATIONS

Chang, Artificial Cells (1972), American Lecture Series Publication No. 828.

*Primary Examiner*—T. K. Page
*Attorney, Agent, or Firm*—Finnegan, Henderson, Farabow, Garrett and Dunner

[57] ABSTRACT

Polyelectrolyte membrane capsules are composed of a semi-permeable membrane and an active material enclosed by it, the membrane being formed of a biocompatible, non-toxic polyacid and a polybase; the polybase is composed of repeating monomer units of the formula (I)

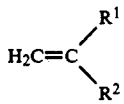

in which $R^1$ and $R^2$ have the indicated meanings.

19 Claims, No Drawings

MICROENCAPSULATION OF BIOLOGICALLY ACTIVE MATERIAL

This application is a continuation of application Ser. No. 07/159,396, filed Feb. 23, 1988 now abandoned.

The immobilization of enzymes or living cell material is extensively known. It is possible by enclosing active cell material in microcapsules, such as is described in, for example, "Artificial Cells" T. M. S. Chang and C. C. Thomas Publ., Springfield Illinois (1972), owing to the compartmentilization with retention of the largest possible surface, for the biological activity of the material to be retained or improved.

Many processes have been described for the encapsulation of cells and cell material, most of which are based on enclosing the cell material in a semipermeable, water-insoluble, biocompatible membrane which is formed by reaction of dissolved polyanionic with polycationic polymers.

German Offenlegungsschrift 3,012,233 describes a process for the encapsulation of tissue or single cells. The cell material is said to be enclosed in a viable and protected state in a membrane which, in order to maintain the normal metabolic functions of the cells, is permeable to nutrients, ions, oxygen and other low molecular weight substances. The material which is to be encapsulated is suspended in a medium which contains a water-soluble substance which can form gel droplets, in order to provide a temporary protective covering for the tissue. Because of the sensitivity of the cell material, it is possible to use only very special buffer media for the reversible gel formation via an electrolyte medium. Preferred substances for the formation of the temporary capsules are natural polysaccharide gum resins which a) are able reversibly to form, when the conditions are changed, for example the pH or on addition of multiply charged cations, such as $Ca^{2+}$, a composition which retains its shape, and which b) are able to form permanent complexes with polybases whose amino groups are able to react with acidic polysaccharide constituents. After formation of the permanent semipermeable membrane, it is possible for the temporary capsule to be dissolved by setting up the conditions under which the substance is liquid. This is particularly necessary when the biologically active material is extremely sensitive and its cell growth or its metabolism is hindered by the numerous crosslinked groups in the polysaccharide resin.

German Offenlegungsschrift 3,209,127 describes a process in which cells are encapsulated by the above-mentioned method in order to obtain metabolic products.

Biologically active material can also be enclosed in proteins having a substantially neutral net charge, as mentioned in European Application 0,129,619. However, this entails problems which are caused, for example, by relatively easy microbiological contamination or restively low reproducibility of the proteins, but especially by the fact that a reversible gel/sol transition is impossible.

European Patent Application 0,188,309 describes a process in which living cell material is enclosed in a biocompatible semipermeable, water-insoluble membrane which is formed by reaction of acrylic-based polycationic and polyanionic polymers. This entails the polyanionic or polyationic acrylic polymer being dissolved in water, and the cell material being suspended therein. The suspension is introduced in the form of drops in to a solution which contains the polycationic or polyanionic acrylic polymers having the opposite electric charge, resulting in the formation of the polymer-polymer complex membrane at the phase boundary.

European Patent Application 0,152,898 describes a process in which an active material, (cells, microorganisms, enzymes, hormones, antibodies, catalysts or substrates) is enclosed in a microcapsule whose membrane is formed by reaction of an anionic or cationic polymer with an ionic polymer having the opposite charge. Utilizable anionic polymers which are disclosed are alginate, carrageenan, hyaluronic acid, carboxymethylcellulose, xanthan, furcellaran and sulfonated organic polymers; and cationic are chitosan, polylysine, polyethylamine and polyvinylamine.

However, none of the polyelectrolyte membrane capsules, or processes for the preparation thereof, described hitherto give any indication of which concentrations thereof, are particularly suitable for meeting the following requirements of polyelectrolyte membrane capsules.

On the one hand, the polyelectrolyte complexes used must themselves, and the membrane formed around the core must, be stable; on the other hand, the polyelectrolytes used must meet the biological and technical processing requirements.

The biological requirements include, for example:
the cell compatibility, the stability of the membrane at the given ionic strength, or the reaction temperature of the polyelectrolytes used.

The technical processing requirements include, for example:
the viscosity of the solution. Thus, it must be possible for the solution to be atomized and for it to form drops of adequate elasticity.

The stability of polyelectrolyte membranes depends on a large number of parameters, for example:
on the charge density, the charge, the molecular weight or the structure (conformation) of the polyelectrolytes.

Although these parameters can be determined subsequently, it is not straightforward to deduce from the idealized individual values the ideal polymer which meets the requirements made above, because the desired properties usually result only from a combination of these parameters.

Surprisingly, polybases for the preparation of polyelectrolyte membrane capsules which meet all the above-mentioned requirements have now been found.

Hence the invention relates to:
polyelectrolyte membrane capsules composed of a semipermeable membrane and of an active material enclosed by it, the membrane being composed of a biocompatible, nontoxic polyacid and a polybase, wherein the poly-base is composed of a polymer formed of repeating monomer units of the formula (I)

in which
$R^1$ is hydrogen or methyl, and $R^2$ is an aminomethyl group, an imidazolyl radical or a radical of the formula (II)

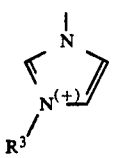

(II)

in which $R^3$ denotes hydrogen, methyl or ethyl, it being possible for monomer units which are linked together also to contain radicals $R^1$ and $R^2$ which are different from one another, and, where appropriate, further hydrophilic, biocompatible monomer units which do not have an electric charge, and, where appropriate, further water-soluble, biocompatible polymers which, where appropriate, are crrosslinked via bridging units with the polymer formed of monomer units of the formula I and, where appropriate, with further hydrophilic, biocompatible monomer units which do not have an electric charge.

The invention also relates to a process for the preparation of the polyelectrolyte membrane capsules according to the invention, to the subsequent modification thereof, for example crosslinking, and to the use thereof for the preparation of products by cell cultures.

The invention is described in detail hereinafter.

Active material is defined, as for example, cells, cell material, microorganisms, enzymes, hormones or even nonbiochemical substances such as substrates or catalysts.

The active material is encapsulated in a manner known per se, as described in, for example, European Published Applications 0,152,898 or 8,188,309. This entails the active material being dissolved or suspended in a 0.1%–10% strength aqueous solution of the polyacid, converted into the form of drops, and then introduced into a 0.1%–10% strength aqueous solution of the polybase, resulting in the formation, at the phase boundary between polyacid and polybase, of the semipermeable membrane which encloses the active material. It is possible, by use of the above-mentioned polybases, to prepare microcapsules having a diameter of 100 to 3000 μm. The drop size can be controlled in a known manner, for example, via the characteristics of the nozzle. The nozzle comprises, for example, an injection needle (internal diameter 0.1-1 mm). This can be inserted concentrically in a hollow cylinder so that it is possible to generate, via the resulting annular slit, a stream of gas which flows tangentially round and pushes off the drops emerging from the nozzle. The drop size decreases as the gas flow rate increases.

The polyacids used, which contain the active material, ought, in the specific case of encapsulation of sensitive biological material, to be biocompatible. Examples of those used for this are polysaccharides such as alginate, carrageenan, carboxymethylcellulose or xanthan.

The polybases of the formula (I) used for the preparation of the polyelectrolyte membrane capsules according to the invention can, if they cannot be bought, be prepared in a straightforward manner.

Solution polymerization of one or, where appropriate, a plurality of various monomers of the formula (I) and, where appropriate, further hydrophilic, biocompatible, electrically neutral monomers such as, for example, N-vinylpyrrolidone, N-vinyl-N-methylacetamide, vinylcaprolactam, acrylic acid or acrylamides results in a polybase which either can be used directly or, where appropriate, can also be mixed with further water-soluble, biocompatible polymers, it being possible for these additionally added polymers to be crosslinked, with the addition of epichlorohydrin, with the polymers constructed of monomer units of the formula (I). Examples of additional water-soluble, biocompatible polymers which can be used are cellulose ethers or condensation products of dicarboxylic acids and diamines.

The polybases are preferably composed of a polymer formed of one or more different monomers of the formula (I) and of a polymeric condensation product of dicarboxylic acids of the formula (IV) and diamenes of the formula (V), the two polymers preferably being crosslinked with epichlorohydrin. This results in the formation of bridging units derived from epichlorohydrin between the two polymers. As a result, these are 2-hydroxypropylene units (—$CH_2$—CHOH-$CH_2$—). Particularly preferred monomers of the formula (I) are polyvinylmenthylimidazole, polyallylamine and polymethallylamine. The dicarboxylic acids used are straight-chain, saturated dicarboxylic acids having 2 to 10 carbon atoms, preferably 5 or 6 carbon atoms, and the diamenes used are oligomeric ethylenediamines having 2 to 5 ethylene units, preferably two ethylene units.

For the preparation of the preferred polybases, first the monomer(s) of the formula (I) is (or are) polymerized in aqueous solution. After the polymerization is complete, the condensation product of dicarboxylic acid (IV) and diamine (V) is added as aqueous solution to the polymer, and crosslinking is carried out with the addition of epichlorohydrin. The condensation product is preferably prepared from equimolar quantities of dicarboxylic acid (IV) and diamine (V). The molar ratio of the polymer comprised of monomer units of the formula (I) to the condensation product is 500–25:1, preferably 50:1, particularly preferably 25:1.

The concentration of the added epichlorohydrin is 0.1 to 0.5 mol-%, (based on the polymer composed of monomers of the formula (I)), preferably 0.2 mol-%, particularly preferably 0.4 mol-%. the molecular weight of the polybases used is 1000–200,000 Dalton. If the polyallylamine or polymethallylamine is used as a monomer of the formula (I), then the molecular weight is preferably 5000–100,000 Dalton. When polyvinylmenthylimidazole is used as a monomer of the formula (I), the molecular weight is preferably 5000–200,000 Dalton.

It is possible according to the invention to enclose biologically active substances, or active materials which are able to produce biologically active substances, in the polyelectrolyte membrane. This membrane permits the transport of a large number of substances, such as nutrients and substrates, to the biologically active substance and is able either to retain selectively the substances produced there or to allow only those to pass (semipermeability). The active material can be, for example, a cell or a cell material or a chemical or biochemical reactant. Examples of cells which can be used are: hybridoma cells or genetically modified cells prepared by means of recombinant DNA technology, or Lymphocytes which are able to product antibodies or microorganisms for the fermentation.

It is also possible to encapsulate microorganisms such as bacteria. It is furthermore possible to encapsulate biologically active compounds such as enzymes, hormones, antibodies or antibiotics, which can be controllably released through the membrane or—for example for catalytic reactions—are retained by the membrane.

The permeability of the membrane can be controlled
a) via the concentrations of the polyacids and polybases used
b) via the pH of the aqueous solution of the polyacids or bases
c) via the molecular weight of the polyacids and polybases used, and via the molecular weight distribution, and
d) via a suitable choice of, in particular, the polybases and the charge density thereon.

Thus, for example, an increase in the polymer concentration usually results in a decrease in the permeability; on the other hand, for example, a content of less than 30 mol-% of monomers having a positive charge results in inadequate capsule stability.

The invention is explained in more detail hereinafter by means of examples.

EXAMPLE 1

294.9 g (3.15 mole) of allylamine hydrochloride are dissolved in 105 ml of water in a 2 l glass flask. The measured pH of this solution is 0. The pH is now adjusted to 4.1 using 4.23 g of 5% strength ammonia solution. A solution of 3.3 g of 2,2'-azobis(2-amidinopropane) dihydrochloride dissolved in 15 ml of water is then added dropwise, and polymerization is carried out at 50° C., passing in nitrogen, for 16 hours. Subsequently a further 3.3 g of 2,2'-azobis(2-amidinopropane) dihydrochloride in 15 ml of water are added dropwise, and polymerization is continued for 4 hours. 288.18 g of the condensation product of 1 mole of adipic acid and 1 mole of diethylenetriamine are now added in the form of a 50% strength aqueous solution to this polymer solution. Subsequently, 5.829 g (0.06 mole) of epichlorohydrin are added as a 5% strength ethanolic solution, and crosslinking is carried out at 50° C. for 30 minutes. After this time a further 5.829 g (0.06 mole) of epichlorohydrin are added as a 5% strength ethanolic solution, and crosslinking is continued at 5020 C. for 30 minutes. The polymer is now adjusted to the final concentration of 40% with water.

The reaction was followed by measuring the K value in 1% strength solution:
K value (before polymerization) $7.6 \times 10^3$
K value (after polymerization) $9.5 \times 10^3$
K value (after crosslinking) $18.3 \times 10^3$

EXAMPLE 2

In analogy to Example 1, a product is obtained from 294.9 g (3.15 mole) of allylamine hydrochloride and 323.75 g (1.25 mole) of the condensation product of 1 mole of suberic acid and 1 mole of diethylenetriamine after subsequent crosslinking with epichlorohydrin in the form of a 50% strength aqueous solution.

EXAMPLE 3

149.8 g (1.59 mole) of allylamine hydrochloride are introduced into a 1 l glass flask and are dissolved in 54.4 g of water. The pH is then adjusted to 4.1 using 7.78 g of 5% strength ammonia solution. 1.7 g of 2,2'-azobis(2-amidinopropane) dihydrochloride dissolved in 8 ml of water are now added, and the reaction solution is heated at 50° C., while passing in nitrogen, and polymerized for 16 hours. A further 1.7 g of 2,2'-azobis(2-amidinopropane) dihydrochloride dissolved in 8 ml of water are then added and polymerization is carried out at 50° C. to 60° C. for a further 4 hours. 144.76 g of this aqueous polymer solution are taken, and 457.4 g of the condensation product of 1 mole of adipic acid and 1 mole of diethylenetriamine are added as a 50% strength aqueous solution. After a reaction time of 60 minutes at 50° C. to 60° C.., crosslinking is carried out at by dropwise addition of 37 g of 5% strength ethanolic epichlorohydrin solution at 50° C. for 30 minutes. After further crosslinking with another 37 g of 5% strength ethanolic epichlorohydrin solution, the pH of the reaction solution is adjusted to a pH of 7.5 using 70.7 g of concentrated hydrochloric acid, and then the total concentration is adjusted to 40% using 30.4 g of water. The course of the polymerization was followed by measuring the K value:
K value (before polymerization) $8.6 \times 10^3$
K value (after polymerization) $9.9 \times 10^3$
K value (after crosslinking) $21.6 \times 10^3$

EXAMPLE 4

In analogy to Example 2, 149.8 g (1.59 mole) of allylamine hydrochloride are polymerized and crosslinked with 178.8 g of the condensation product of 1 mole of sebacic acid and 1 mole of diethylenetriamine, with the addition of epichlorohydrin. A 40% strength aqueous solution is obtained.

EXAMPLE 5

294.9 g (3.15 mole) of allylamine hydrochloride are introduced into 105 ml of water in a 2 l glass flask, and the pH is adjusted to 4.1 using 10.6 g of 5% strength ammonia solution. 3.3 g of 2,2'-azobis(2-amidinopropane) dihydrocloride dissolved in 15 ml of water are now added, and the mixture is heated at 50° C., while passing in nitrogen. Polymerization is carried out at this temperature for 16 hours. A further 3.3 g of 2,2'-azobis(2-amidinopropane) dihydrochloride dissolved in 15 ml of water are then added and polymerization is continued at 50° C. for 4 hours. 341.4 g (0.623 mole) of a condensation product of 1 mole of adipic acid and 1 mole of triethylenetetriamine are now added in the form of a 50% strength aqueous solution to this polymerization solution and, after a reaction time of 60 minutes at 50° C. to 60° C., crosslinking is carried out by dropwise addition of 116.58 g of a 5% strength ethanolic epichlorohydrin solution at 50° C. for 30 minutes. After a further 30 minutes, another 116.58 g of 5% strength ethanolic epichlorohydrin solution are added, and crosslinking is carried out at for a further 30 minutes. The sample is then adjusted to a content of 40% of polymer. The reaction was followed by measuring the K value in 1% strength aqueous solution:
K value (before polymerization) $8.1 \times 10^3$
K value (after polymerization) $9.8 \times 10^3$
K value (after crosslinking) $22 \times 10^3$

EXAMPLE 6

In analogy to Example 5, 294.9 g (3.15 mole) of allylamine hydrochloride are polymerized and crosslinked with 161.35 g (0.623 mole) of a condensation product of 1 mole of suberic acid and 1 mole of diethylenetriamine, with the addition of epichlorohydrin. The sample is then adjusted to a content of 40% of polymer.

EXAMPLE 7

74.9 g (0.8 mole) of allylamine hydrochloride dissolved in 27.2 ml of water are introduced into a 2 l glass flask, and then the pH is adjusted to 4.1 using 7.78 g of 5% strength ammonia solution. 0.85 g of 2,2'-azobis(2-amidinopropane) dihydrocloride dissolved in 8 ml of water are now added, and polymerization is carried out at 55° C., passing in nitrogen, for 16 hours. A further 0.85 g of 2,2'-azobis(2-amidinopropane) dihydrochloride is then added, and polymerization is continued at 55° C. for 3 hours. 457.43 g of a 50.5% strength aqueous solution of a condensation product of 1 mole of adipic acid and 1 mole of diethylenetriamine are now added and, after a reaction time of 60 minutes at 50° C.–55° C., 37 g of a 5% strength ethanolic epichlorohydrin solution are added, and crosslinking is carried out for 20 minutes. A further 37 g of a 5% strength ethanolic epichlorohydrin solution are then added, and crosslinking is continued for 30 minutes. The pH is then adjusted to 7.5 using 70.7 g of concentrated hydrochloric acid, and the substance content is adjusted to 40% using 30.4 ml of water.

The reaction was followed by the K values measured in 1% strength aqueous solution:

K value (before polymerization) $8.0 \times 10^3$
K value (after polymerization) $20.8 \times 10^3$
K value (after crosslinking) $34.7 \times 10^3$

EXAMPLE 8

294.9 g (3.15 mole) of allylamine hydrochloride are dissolved in 105 ml of water in a 1 liter glass flask and, while cooling, 126.39 g (1.276 mole) of N-vinyl-N-methylacetamide are added. The pH is then adjusted to 4 using 10.5 g (0.154 mole) of concentrated ammonia. 10.53 g of 2,2'-azobis(2-amidinopropane) dihydrocloride dissolved in 48 g of water are now added. While passing in nitrogen, the mixture is heated to an internal temperature of 50° C., and polymerization is completed in 16 hours. This entailed a further 10.53 g of 2,2'-azobis(2-amidinopropane) dihydrochloride dissolved in 48 g of water being added after 4 hours, and the pH being readjusted with concentrated ammonia to pH 4. 660.38 g of 63.3% strength solution of copolymer are obtained.

EXAMPLE 9

294.9 g (3.15 mole) of allylamine hydrochloride are dissolved in 105 ml of water in a 1 liter glass flask and, while cooling, 126.39 g (1.345 mole) of N-vinylimidazole are added. 10.53 g of 2,2'-azobis(2-amidinopropane) dihydrocloride dissolved in 48 g of water are then added. The mixture is heated to 50° C., while passing in nitrogen, and polymerization at this temperature for 16 hours. After polymerization for 4 hours a further 10.53 g of 2,2'-azobis(2-amidinopropane) dihydrochloride dissolved in 48 g of water were added. 645 g of 64.3% strength aqueous copolymer solution are obtained.

EXAMPLE 10

1443 g (10 mole) of 1-vinyl-3-methylimidazolium chloride and 56 g (0.5 mole) of 1-vinyl-2-pyrrolidone are dissolved in 3.8 l of water which contain 38 g of potassium peroxodisulfate as initiator in a 4 liter glass flask. The mixture is polymerized at 60° C., under nitrogen for 6 h. A clear yellow-brown 40% strength solution with a neutral pH is obtained. The K value is 60.

EXAMPLE 11

PREPARATION OF MEMBRANE CAPSULES / ENCLOSURE OF CELLS

A suspension of hybridoma cells is diluted 1:1 (ratio by mass) with a 4% by weight λ-carrageenan solution (manufactured by Sigma Chemie GmbH, Munich) in Dulbecco's medium. Drops are formed from the solution through a nozzle. The nozzle comprises an injection needle of internal diameter 0.2 mm and external diameter 0.4 mm. It is inserted concentrically into a hollow cylinder so that it is possible to generate, through the resulting annular slit, a tangential stream of air which pushes off the drops emerging from the injection needle. The drop sizes depend on the air velocity and are 100 μm–3000 μm. The drops fall into a solution of the polybase. A 0.5% by weight solution of the base prepared as in Example 1 is used. There is immediate complexation to form a polyelectrolyte complex membrane. The capsules are washed several times in a buffer solution and then transferred into a culture medium and stored in an incubator.

EXAMPLE 12

Drops of cell suspension are prepared in analogy to Example 11. They fall into a polybase. A 2% by weight solution of the polybase which was prepared as in Example 10 is used. The capsules are further treated in analogy to Example 11.

EXAMPLE 13

The capsules prepared as in Example 12 are cultivated in an incubator. The cell populations increase and, after 20 days, the capsules are completely filled with cells. The cells produce about 2 μg of antibody per capsule, i.e. about 1.1 mg of antibody per ml of reactor volume.

EXAMPLE 14

The capsules prepared as in Example 11 are cultivated in an incubator. The capsules allow the produced antibodies to pass through. After 18 days about 0.7 mg of antibodies was discharged per ml of culture medium.

EXAMPLE 15

1 ml of an antibody solution (0.091 mg of IgG factor VIII/type 1, manufactured by Calbiochem GmbH) in phosphate buffer, pH 7.4 (0.00205 M $Na_2HPO_4$, 0.0045 M $NaH_2PO_4$), is mixed with 1 ml of a 4% by weight λ-carrageenan solution (manufactured by Sigma Chemie GmbH, Munich). The solution is added dropwise from a disposable syringe (injection needle diameter 0.4 mm) to 100 ml of a 0.5% by weight solution of the polybase from Example 1. After 3 minutes, the supernatant solution of the polybase was decanted off from the microcapsules, which were then washed three times with phosphate buffer, pH 7.4, and suspended in 10 ml of the buffer.

Microcapsules are prepared analogously using the polybase from Example 10. However, the concentration of the polybase is 2% by wight. After 20 minutes, the supernatant solution of the polybase is decanted off from the microcapsules, which are then washed once with phosphate buffer, pH 7.4, and suspended in 10 ml of the buffer.

After defined times (see table) a 1 ml sample of each of the suspensions is taken, and its antibody content (% by weight) is determined in an enzyme immunoassay (ELISA [Enzyme-Linked Immunosorbent Assay], Behringwerke AG, Marbug). Release of the total amount of antibody from the microcapsules is taken as 100%.

|  | 10 minutes | 20 hours | 10 days |
|---|---|---|---|
| Polybase from Example 1 | <0.1% | 100% | 100% |
| Polybase from Example 10 | <0.1% | <0.1% | <0.1% |

We claim:

1. Polyelectrolyte membrane capsules composed of a semi-permeable membrane and of a biologically active material enclosed by it, the membrane being composed of a biocompatible, nontoxic polyacid and a polybase, wherein the poly-base is composed of a polymer formed of repeating monomer units of the formula (I)

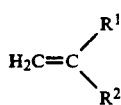

in which
$R^1$ is hydrogen or methyl, and
$R^2$ is an aminomethyl group, an imidazolyl radical or a radical of the formula (II)

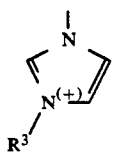

in which
$R^3$ denotes hydrogen, methyl or ethyl, it being possible for monomer units which are linked together also to contain radicals $R^1$ and $R^2$ which are different from one another, and, where appropriate, further hydrophilic, biocompatible monomer units which do not have an electric charge,
and, where appropriate, further water-soluble, biocompatible polymers which, where appropriate, are crrosslinked via bridging units with the polymer formed of monomer units of the formula I and, where appropriate, with further hydrophilic, biocompatible monomer units which do not have an electric charge.

2. Polyelectrolyte membrane capsules as claimed in claim 1, wherein the polybase is composed of a polymer formed from repeating monomer units of the formula (I) as shown in claim 1 and further water-soluble, biocompatible polymers which are, where appropriate, crosslinked via bridging units with the polymer formed of monomer units in the formula I.

3. Polyelectrolyte membrane capsules as claimed in claim 1, wherein the polybase is comprised of a polymer formed of repeating monomer units of the formula (I) as shown in claim 1 and further hydrophilic, biocompatible monomer units which have no electric charge.

4. Polyelectrolyte membrane capsules as claimed in claim 1, wherein the polybase is composed of a polymer formed of repeating monomer units of the formula (I) as shown in claim 1 and further hydrophilic, biocompatible monomer units which have no electric charge, and further water-soluble, biocompatible polymers which are, where appropriate, crosslinked via bridging units with the polymer formed of monomer units of the formula I and, where appropriate, with further hydrophilic, biocompatible monomer units which have no electric charge.

5. Polyelectrolyte membrane capsules as claimed in claim 2, wherein a condensation product of dicarboxylic acids of the formula (IV)

$$HOOC-(CH_2)_n-COOH \qquad (IV)$$

in which n is 0 to 8, and amines of the formula (V)

$$H_2N-CH_2-(CH_2-NH-CH_2)_m-CH_2-NH_2 \qquad (V)$$

in which m is 1 to 4, is used as further water-soluble, biocompatible polymers.

6. Polyelectrolyte membrane capsules as claimed in claim 5, wherein the polymer formed of repeating monomer units of the formula (I) as shown in claim 1 and the condensation products of the compounds of the formula (IV) and (V) as shown in claim 5 are crosslinked with bridging units derived from epichlorohydrin.

7. Polyelectrolyte membrane capsules as claimed in claim 3, wherein N-vinylpyrrolidone and/or N-vinyl-N-Methylacetamide and/or vinylcaprolactam are used as further hydrophilic, biocompatible monomer units which have no electric charge.

8. Polyelectrolyte membrane capsules as claimed in claim 3, wherein the molar proportion of the hydrophilic biocompatible monomer units which have no electric charge is 0%–70% based on the total molecular weight of the polybase.

9. Polyelectrolyte membrane capsules as claimed in claim 2, wherein the molar proportion of the water-soluble, biocompatible polymers is 0%–50% based on the total molecular weight of the polybase.

10. Polyelectrolyte membrane capsules as claimed in claim 1, wherein a polymer formed of methallylamine or allylamine monomers is used as polybase.

11. Polyelectrolyte membrane capsules as claimed in claim 10, wherein the polybase has a molecular weight of 5000–100,000 Dalton.

12. Polyelectrolyte membrane capsules as claimed in claim 1, wherein a polymer formed of vinylmethylimidazole monomers of the formula (III)

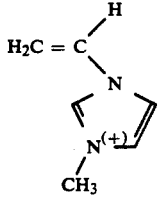

is used as polybase.

13. Polyelectrolyte membrane capsules as claimed in claim 12, wherein the polybase has a molecular weight of 5000–200,000 Dalton.

14. Polyelectrolyte membrane capsules as claimed in claim 1, wherein enzymes, cells or cell material is used as the biologically active material.

15. A process for the preparation of polyelectrolyte membrane capsules as claimed in claim 1, in which a suspension or solution of the biologically active material in an aqueous solution of a water-soluble, non-toxic, biocompatible polyacid is prepared, and this aqueous suspension or solution is introduced in the form of drops into an aqueous solution of a water-soluble polymeric base, and in which the polyacid and the polybase react together at the phase boundary, and a water-soluble, semipermeable polymer-polymer complex membrane is formed around the active material, which comprises the polybase being a polymer comprised of repeating monomer units, of the formula (I) as shown in claim 1, it being possible for monomer units which are linked together to contain radicals $R^1$ and $R^2$, as defined in claim 1, which are different from one another, and, where appropriate, further hydrophilic, biocompatible monomer units which have no electric charge, and, where appropriate, contains further water-soluble, biocompatible polymers which are, where appropriate, cross-linked via bridging units with the polymer formed of monomer units of the formula I and, where appropriate, with further hydrophilic, biocompatible monomer units which have no electric charge.

16. A process for preparing products from biologically active material comprising cultivating the biologically active material in the polyelectrolyte membrane capsules as claimed in claim 1.

17. A process as claimed in claim 16, wherein said biologically active material comprises enzymes, cells or cell material.

18. A process as claimed in claim 17, wherein the products prepared are formed in the polyelectrolyte membrane capsules and are retained within the capsules.

19. A process as claimed in claim 17, wherein the products prepared are formed in the polyelectrolyte membrane capsules and can be released from the capsules.

* * * * *

UNITED STATES PATENT AND TRADEMARK OFFICE
CERTIFICATE OF CORRECTION

PATENT NO. : 5,100,673
DATED : March 31, 1992
INVENTOR(S) : Hubert Bader et al.

It is certified that error appears in the above-identified patent and that said Letters Patent is hereby corrected as shown below:

Claim 1, column 9, line 47, change "crrosslinked" to --crosslinked--.

ON THE TITLE PAGE:

Inventors, top line, change "Herbert Bader" to --Hubert Bader--.

Inventors, line 2, after "Diether Ruppel" insert --Frankfurt am Main--.

Signed and Sealed this

Second Day of November, 1993

Attest:

BRUCE LEHMAN

Attesting Officer

Commissioner of Patents and Trademarks